(12) United States Patent
Dechelette et al.

(10) Patent No.: US 10,893,890 B2
(45) Date of Patent: Jan. 19, 2021

(54) POLYAXIAL BONE FIXATION ASSEMBLY (71) Applicant: NEOSTEO, Nantes (FR)

(72) Inventors: Maxime Dechelette, Petit Mars (FR); Sylvain Sorin, Nantes (FR)

(73) Assignee: NEOSTEO, Nantes (FR)

( * ) Notice: Subject to any disclaimer, the term of this patent is extended or adjusted under 35 U.S.C. 154(b) by 0 days.

(21) Appl. No.: 16/345,973

(22) PCT Filed: Oct. 30, 2017

(86) PCT No.: PCT/FR2017/052982
§ 371 (c)(1),
(2) Date: Apr. 29, 2019

(87) PCT Pub. No.: WO2018/083407
PCT Pub. Date: May 11, 2018

(65) Prior Publication Data
US 2020/0054363 A1    Feb. 20, 2020

(30) Foreign Application Priority Data

Nov. 4, 2016 (FR) ...................... 16 60679

(51) Int. Cl.
*A61B 17/70* (2006.01)
*A61B 17/86* (2006.01)
(Continued)

(52) U.S. Cl.
CPC ...... *A61B 17/7037* (2013.01); *A61B 17/7032* (2013.01); *A61B 17/8605* (2013.01); *A61B 17/88* (2013.01); *A61B 2017/564* (2013.01)

(58) Field of Classification Search
CPC ............ A61B 17/7037; A61B 17/7032; A61B 17/8605; A61B 17/88; A61B 17/088;
(Continued)

(56) References Cited

U.S. PATENT DOCUMENTS 8,652,183 B1 * 2/2014 Truman ............. A61B 17/8038
606/281
2006/0009771 A1   1/2006 Orbay et al.
(Continued)

FOREIGN PATENT DOCUMENTS

FR    8652183    2/2014

OTHER PUBLICATIONS

International Search Report dated Nov. 12, 2017.

*Primary Examiner* — Pedro Philogene
(74) *Attorney, Agent, or Firm* — Ipsilon USA, LLP (57) ABSTRACT

A polyaxial bone fastener assembly (1) comprising a plate (2) with at least one through orifice (3), and at least one fastener screw (4) for fastening the plate (2) to a bone, the body (6) of the screw (4) being suitable for passing through the orifice (3), and its head (5) being suitable for being retained in the orifice (3) of the plate (2) by bearing contact between complementary male and female spherical surfaces (7, 8), the female spherical surface (8) that is arranged in the orifice (3) of the plate (2) forming a seat within which the male spherical surface (7) is suitable for coming to bear when the screw (4) is inserted in the orifice (3).

On going from the bottom face (22) towards the top face (21) of the plate (2), the bore of the orifice (3) in the plate (2) comprises: an inner collar (9); a cylindrical portion (10); and the seat-forming female spherical surface (8); and on going between its male spherical surface (7) and its zone (11) connecting to the body (6) of the screw (4), the head (5) of the associated fastener screw (4) has a threaded portion (12) with a single-start thread, the thread being interrupted in at least two zones (13) in order to enable the inner collar (9) of the orifice (3) in the associated plate (2) to be machined while the screw (4) is being driven to turn inside (Continued)

said orifice (3) until it reaches a position of bearing contact between the male and female spherical surfaces (7, 8).

14 Claims, 5 Drawing Sheets

(51) Int. Cl.
     *A61B 17/88*      (2006.01)
     *A61B 17/56*      (2006.01)

(58) Field of Classification Search
     CPC .............. A61B 17/8033; A61B 17/866; A61B 17/8061; A61B 17/8057; A61B 17/8625; A61B 17/868; A61B 2017/00831; A61B 2017/8655; A61B 2017/564; A61L 31/022; A61L 2430/02
     USPC .................................. 606/246–289, 300–328
     See application file for complete search history.

(56) References Cited

U.S. PATENT DOCUMENTS

| | | | |
|---|---|---|---|
| 2006/0084979 A1* | 4/2006 | Jackson | A61B 17/7037 606/304 |
| 2014/0207194 A1* | 7/2014 | Wolter | A61B 17/8057 606/288 |
| 2016/0015439 A1 | 1/2016 | Wolter | |

* cited by examiner

POLYAXIAL BONE FIXATION ASSEMBLY

RELATED APPLICATION

This application is a National Phase of PCT/FR2017/052982 filed on Oct. 30, 2017, which claims the benefit of priority from French Patent Application Nos. 16 60679, filed on Nov. 4, 2016, the entirety of which are incorporated by reference.

FIELD OF THE INVENTION

The invention relates to a polyaxial bone fastener assembly.

More particularly, the invention relates to a polyaxial bone fastener assembly comprising:
- a plate type support having a top face, a bottom face, and at least one through orifice; and
- at least one fastener screw for fastening the plate to bone material, the screw comprising a head and a threaded body, the body of the screw being insertable from the top face of the plate into the associated orifice in the plate and being suitable for passing through the orifice in order to be screwed into the bone material, and the head being suitable for being held in the associated orifice in the plate by bearing contact between complementary spherical surfaces, one of which is said to be "male" and carried by the head and the other of which is said to be "female" and is provided in the associated orifice in the plate, the female spherical surface forming a seat within which the male spherical surface is suitable for bearing when the screw is inserted in the orifice through the top face of the plate.

PRIOR ART

Among the means used for fastening an osteotomy or a bone fracture, screw-plate systems with locking fastening are in widespread clinical use. The basic principle is always the same: the screw becomes anchored in the bone via its distal thread, while the head thread becomes blocked in a through orifice in the plate. This blocking is referred to as "locking".

This leads to a single-unit screw and plate assembly that improves retention of bone fragments, in particular in terms of fatigue. Locking systems are thus less subject to screws migrating as a result of disengaging from the plate due to micromovements. Bone consolidation is thus enhanced since the implant acts as a bone splint until partial and then total consolidation.

There are two locking fastener technologies:
- monoaxial fastening: the screw can be inserted along a fixed angle only, which angle is determined using a drill jig that co-operates with the orifice in the plate; and
- polyaxial fastening: the screw can be inserted and locked in any desired angular position lying within a circular cone having as its apex the center of rotation in the orifice in the plate.

For complex fractures or osteotomies involving a plurality of fragments of locations that may be various, or because of space requirements (to ensure that the plate is not too thick with monoaxial fastening at a considerable angle relative to the remainder of the plate), the use of multi-axial fastening is essential.

Multi-axial fastening can be implemented using two general principles:

The thread of the head of the screw can co-operate with tapping in an intermediate part that is itself securely mounted to the plate and that is movable enabling the screw, once mounted in this intermediate part, to be pointed in various directions. This is often a ball joint. This results in a three-part assembly, as shown by way of example in patents FR 2 792 185 or US 2011/0172666.

The weak point of this principle, apart from the number of parts, lies in the extra thickness needed for the plate in order to house the intermediate part. It can also sometimes happen that the intermediate part becomes expelled under the effect of the locking torque.

The thread of the head of the screw co-operates with tapping in a plate. There is no mechanical abutment, the threads becoming jammed together by deformation until the system is completely jammed, e.g. as shown in international application WO 2013/059090.

Document US 2014/0207194 also shows such a solution.

The weak point of that principle is the phenomenon of seizing (known in orthopedics as "cold welding"), which can make it impossible to extract the screw, which can lengthen the time required for operation, which can lead to heating, to bone necroses, and to metal debris being abandoned in the patient's body if the screw needs to be extracted by drilling. Often, it is necessary to use a torque screwdriver that serves to stop tightening before the seizing torque is reached.

Nevertheless, such instruments require maintenance, calibration, and are much more expensive to produce than a standard screwdriver. In addition, with a bone that is sclerotic, it can happen that the screwdriver acts prematurely to prevent locking of the screw.

In addition, fastenings performed using that principle are less secure in the monoaxial position (no degree of freedom relative to the axis of the orifice), because there is no abutment. It is thus not unusual to cause the screw to pass through the plate while attempting to lock it.

Furthermore, at very large angles, the head of the screw tends to project from the plate.

Finally, since the threads are damaged very greatly, it is sometimes not possible to remove the screw and then lock it once more in the housing, unlike a fastening where the thread of the head and the tapping of the plate match and where there is an abutment.

The problems encountered with those two principles contribute to multi-axial fasteners having the reputation as being not as strong as monoaxial fasteners, in particular in terms of locking torque.

OBJECTS AND SUMMARY

An object of the invention is to propose a polyaxial bone fastener assembly of two-part design that does not require a torque tool for driving it.

To this end, the invention provides a polyaxial bone fastener assembly comprising:
- a plate type support having a top face, a bottom face, and at least one through orifice; and
- at least one fastener screw for fastening the plate to bone material, the screw comprising a head and a threaded body, the body of the screw being insertable from the top face of the plate into the associated orifice in the plate and being suitable for passing through the orifice in order to be screwed into the bone material, and the head being suitable for being held in the associated orifice in the plate by bearing contact between complementary spherical surfaces, one of which is said to be "male" and carried by the head and the other of which is said to be "female" and is provided in the associated orifice in the plate, the female spherical surface forming a seat within which the male spherical surface is suitable for bearing when the screw is inserted in the orifice through the top face of the plate;

the assembly being characterized in that the bore of the orifice, or of at least one of the orifices, in the plate and that is suitable for being associated with a fastener screw comprises, going from the bottom face towards the top face of the plate, at least one inner collar, a cylindrical portion, and the seat-forming female spherical surface, and in that the head of the associated fastener screw, or of at least one of the associated fastener screws, comprises, between its male spherical surface and its zone for connection to the body of the screw, a threaded portion having a single-start thread, the thread being interrupted in at least two zones that are spaced apart from each other around the head, each interruption zone in the thread providing at least one cutting edge suitable for machining, preferably tapping, the inner collar in the associated orifice of the plate while the screw is being driven to turn inside said orifice until reaching a position of bearing contact between the male and female spherical surfaces.

The presence of a mechanical abutment formed by the bearing contact between the male and female spherical surfaces makes it possible in reliable manner to control the screw tightening that results from co-operation between the threaded portion of the screw head and the collar of the orifice. The screw is thus a compression screw that is lockable in the plate. When the plate is in the locked state, the screw enables the plate to be put into compression against the bone material. Specifically, the screw head is provided with two distinct zones, one having an abutment function and the other a function of engaging with the collar. The screw head thus constitutes both a member for locking in the plate and also a member for compressing the plate against bone material independently of its angular position in the plate. The design of the assembly also makes it possible for the assembly to be assembled and disassembled several times. Such an assembly can also be used with non-locking compression screws.

In an embodiment of the invention, the thread of the threaded portion of the screw head presents, going from the top of the screw head towards its zone connected to the screw body, a thread root defining a body of cylindrical shape followed by a body of conical shape.

In an embodiment of the invention, the thread of the threaded portion of the screw head presents, going from the top of the screw head towards its zone connected to the screw body, a thread crest defining a body of cylindrical shape or of cylindrical-conical shape.

In an embodiment of the invention, the pitch of the threaded portion of the screw head is less than or equal to the pitch of the threaded portion of the screw body.

This results in an improvement in the engagement between the threaded portion of the screw and the inner collar of the associated orifice in the plate.

In an embodiment of invention, the inner collar of the orifice in the plate presents, once machined by the head of the associated fastener screw, a groove that is helical.

In an embodiment of the invention, each cutting edge extends over the full height of the threaded portion of the screw head.

In an embodiment of the invention, the diameter of the hole defined by the inner collar is less than the outside diameter of the threaded portion of the screw head over at least a fraction of the length of said threaded portion measured along the longitudinal axis of the screw.

In an embodiment of the invention, the fastener screw, in its end-of-stroke position inside the associated orifice of the plate, is in bearing contact via the male spherical surface of the screw head with the female spherical surface of said orifice, and is in screw engagement via the threaded portion of the screw head with the inner collar of said orifice.

In an embodiment of the invention, the seat-forming female spherical surface of the orifice, or of at least one of the orifices, in the plate is a concave spherical surface with its concave side facing towards the top face of the plate in order to define a housing of generally hemispherical shape.

In an embodiment of the invention, the top of the screw head is provided with a prismatic axial socket. This socket serves to receive a tool for driving turning of the screw.

In an embodiment of the invention, the plate and the or at least one of the fastener screw(s) are made of the same material, preferably the same metal or the same metal alloy.

In an embodiment of the invention, the male spherical surface carried by the head is dimensioned to be received in the thickness of the plate inside the through orifice in the plate in an end-of-stroke bearing position between the male spherical surface of the head and the female spherical surface of the plate. This housing of the spherical surface of the screw head in the thickness of the plate is independent of the angular position of the screw inside the through orifice in the plate.

In an embodiment of the invention, the thickness of the collar is less than 1 millimeter (mm).

In an embodiment of the invention, the total thickness of the plate is less than 3 mm.

BRIEF DESCRIPTION OF THE DRAWINGS

The invention can be well understood on reading the following description of embodiments given with reference to the accompanying drawings, in which.

DETAILED DESCRIPTION

As mentioned above, the invention provides a polyaxial bone fastener assembly 1 comprising a plate 2 that can be positioned to bear against a bone and at least one fastener screw 4 for fastening the plate 2 to the bone. The plate 2 may have a wide variety of shapes, it may be plane, T-shaped, L-shaped, or of some other shape. In the example shown, the plate 2 is a plane plate made of a metal alloy that is the same as the alloy used for the fastener screw 4. In a variant, the plate 2 could be made of a metal alloy that is different from the alloy used for the fastener screw 4.

The plate 2 has a top face 21, a bottom face 22 opposite from the top face and suitable for being positioned to press against the bone, and at least one through orifice 3. In the example shown, the plate 2 has only one through orifice 3 in order to simplify the drawings. Nevertheless, it could have a plurality of orifices without going beyond the ambit of the invention.

The screw 4 for fastening the plate 2 to bone material 20 comprises a head 5 and a threaded body 6. The body 6 is connected to the head 5 via a connection zone 11 that is not threaded in this example and that is shown as being cylindrical. The body 6 of the screw 4 can be inserted from the top face 21 of the plate 2 into the through orifice 3 in the plate 2 in order to be screwed into the bone material 20, and the head 5 is suitable for being retained in the orifice 3 of the plate 2 by bearing contact between complementary spherical surfaces 7 and 8, where the surface 7 is said to be "male" and is carried by the head 5, and the other surface 8 is said to be "female" and is formed in the orifice 3 of the plate 2. These complementary male and female spherical surfaces 7 and 8 are smooth surfaces in their zones suitable for coming into bearing contact. Thus, these male and female complementary spherical surfaces do not have any threads in their zones suitable for coming into bearing contact when the screw is inserted in the associated orifice in the plate. The female spherical surface 8 forms a seat within which the male spherical surface 7 is suitable for coming to bear when the screw 4 is inserted in the orifice 3 via the top face 21 of the plate 2. This female spherical surface 8 is a concave spherical surface having its concave side facing towards the top face 21 of the plate 2 in order to define a housing that is generally hemispherical in shape. The radius of this female spherical surface 8 is substantially equal to the radius of the male spherical surface, ignoring the clearance that is necessary for inserting the female spherical surface in the male spherical surface. The presence of spherical surfaces enables the screw to be pointed at any angle inside the orifice 3 in the plate while maintaining bearing contact between said surfaces.

On going from the top face 21 towards the bottom face 22 beyond the female spherical surface 8 the bore of the orifice 3 passing through the plate 2 also has: a cylindrical portion or counterbore; followed by an inner collar 9 or inner radial circular lip that performs a function described below. The thickness of the collar 9 is generally less than 1 mm, and is preferably close to 0.2 mm. The total thickness of the plate 2 is preferably less than 3 mm.

The top 17 of the screw head 5 is provided with a prismatic axial socket 16 serving to receive a tool for turning the screw. Between its male spherical surface 7 and its zone 11 for connection to the body 6 of the screw 4, the head 5 of the fastener screw 4 includes a threaded portion 12. On going from the top 17 of the screw head 5 towards its zone 11 for connection to the screw body 6, the thread on this threaded portion 12 of the screw head 5 presents a thread root 121 defining a body of cylindrical shape followed by a body of conical shape. The angle α formed by the thread root in the conical portion relative to the longitudinal axis of the screw preferably lies in the range 5° to 60°. On going from the top 17 of the screw head 5 towards its zone 11 for connection to the screw body 6, the thread of the threaded portion 12 of the screw head 5 presents a thread crest 122 defining a body of cylindrical shape or of cylindrical-conical shape. The angle β formed by the thread crest of the conical portion relative to the longitudinal axis of the screw preferably lies in the range 5° to 80°. The pitch of the threaded portion 12 of the screw head 5 is less than or equal to the pitch of the threaded portion of the screw body 6. This results in the plate being pressed against the bone and provides better engagement of the threaded portion of the screw in the collar, which engagement is described below. The thread of this threaded portion 12 of the screw head 5 is a single-start thread. This thread is interrupted in at least two zones 13 that are spaced apart from one another around the head 5. In the example shown, these interruption zones 13 are three in number and they are spaced apart from one another by 120°. In the presence of two interruption zones, they should preferably be provided so as to be diametrically opposite. Independently of the number of interruption zones, each interruption zone 13 of the thread forms at least one cutting edge 14 suitable for tapping the inner collar 9 in the orifice 3 of the plate 2 while the screw is being driven to turn inside said orifice and until reaching a position of bearing contact between the male and female spherical surfaces 7 and 8. Thus, the collar 9 in the orifice 3 of the plate 2 presents a helical groove 15 once it has been machined by the head of the associated fastener screw acting as a tap. In its end-of-stroke position inside the orifice 3 of the plate 2, the fastener screw 4 is thus in bearing contact via the male spherical surface 7 of the screw head with the female spherical surface 8 of said orifice 3, and via the threaded portion 12 of the screw head 5 it is in screw engagement with the inner collar 9 of said orifice 3. In order to enable the collar to be machined in this way by the threaded portion of the screw, the diameter of the hole defined by the inner collar 9 is less than the outside diameter of the threaded portion 12 of the screw head 5 over at least a fraction of the length of said threaded portion 12 as measured along the longitudinal axis of the screw 4.

In the example shown, each cutting edge 14 extends over the full height of the threaded portion 12 of the screw head 5. Likewise, in the example shown, between its top and its threaded portion 12, the screw head includes an outer radial swelling or protuberance or excrescence forming an outer peripheral collar, the outer circumferential edge of the collar forming the male spherical surface 7, which is thus constituted by the convex outer surface of the spherical portion lying between two parallel planes orthogonal to the longitudinal axis of the screw.

Figure 1:
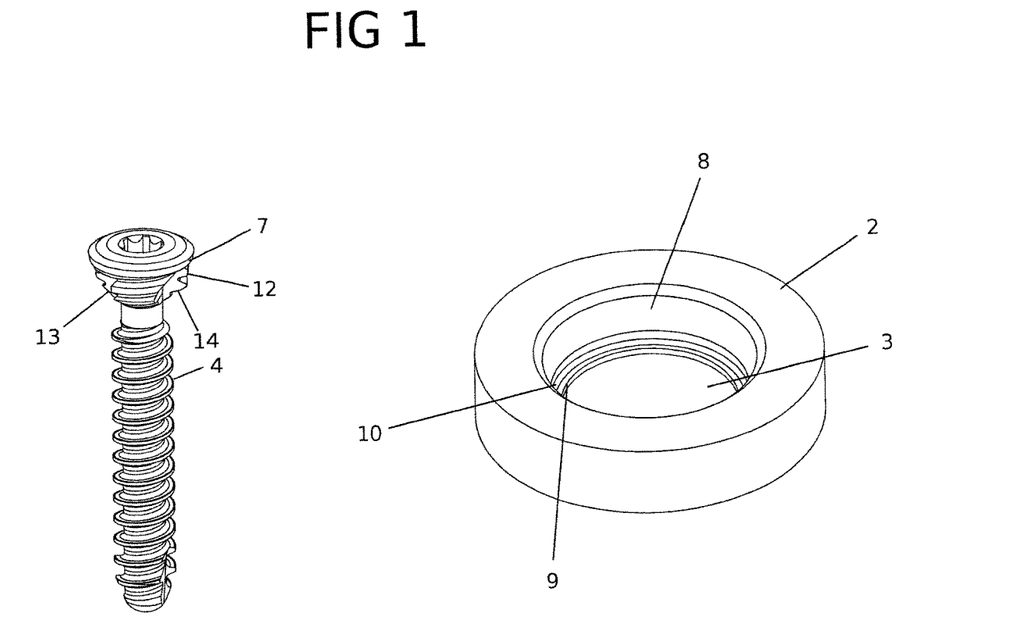
FIG. 1 is a perspective view of a screw and a plate with a through orifice.
Figure 2:
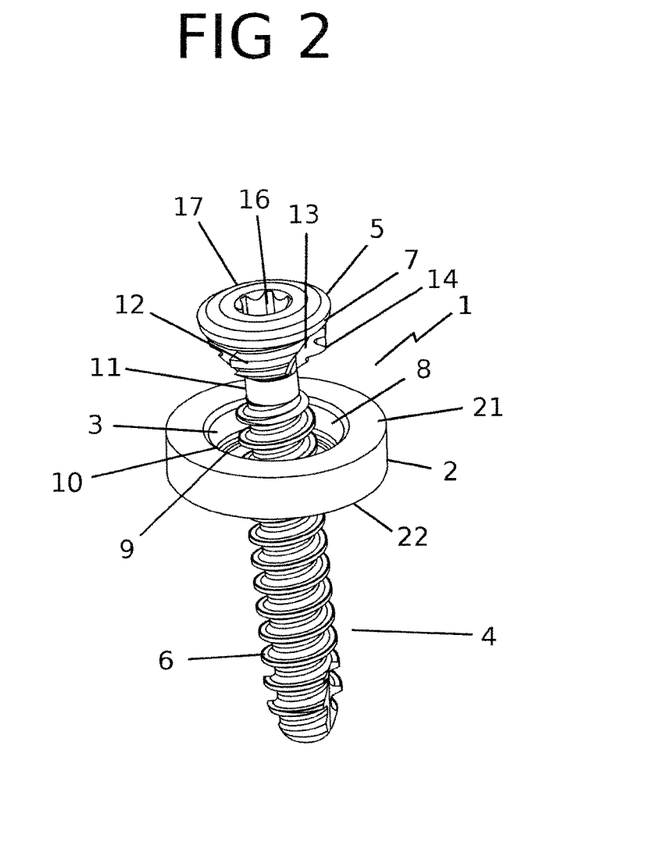
FIG. 2 is a perspective view of a screw when partially inserted in the orifice in a plate.
Figure 3:
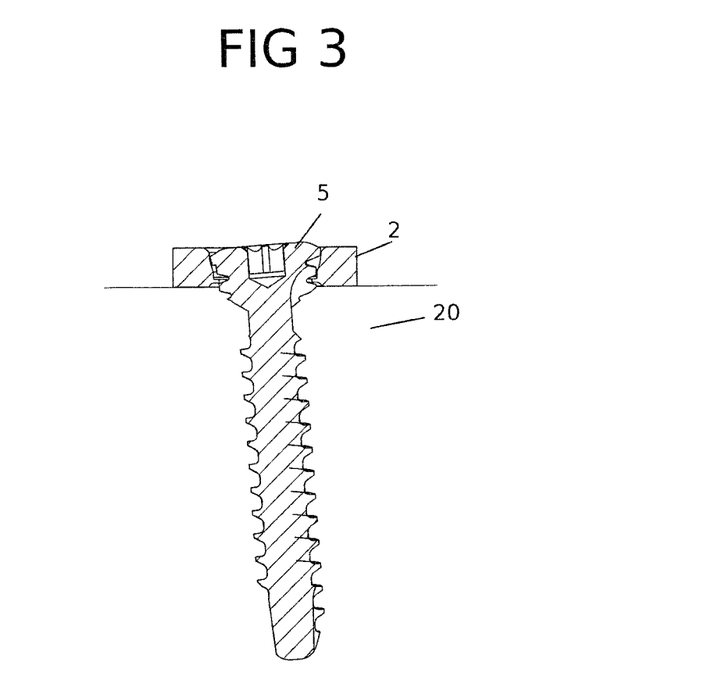
FIG. 3 is a section view of a screw when partially inserted in the orifice in a plate, during a screwdriving operation.
Figure 4:
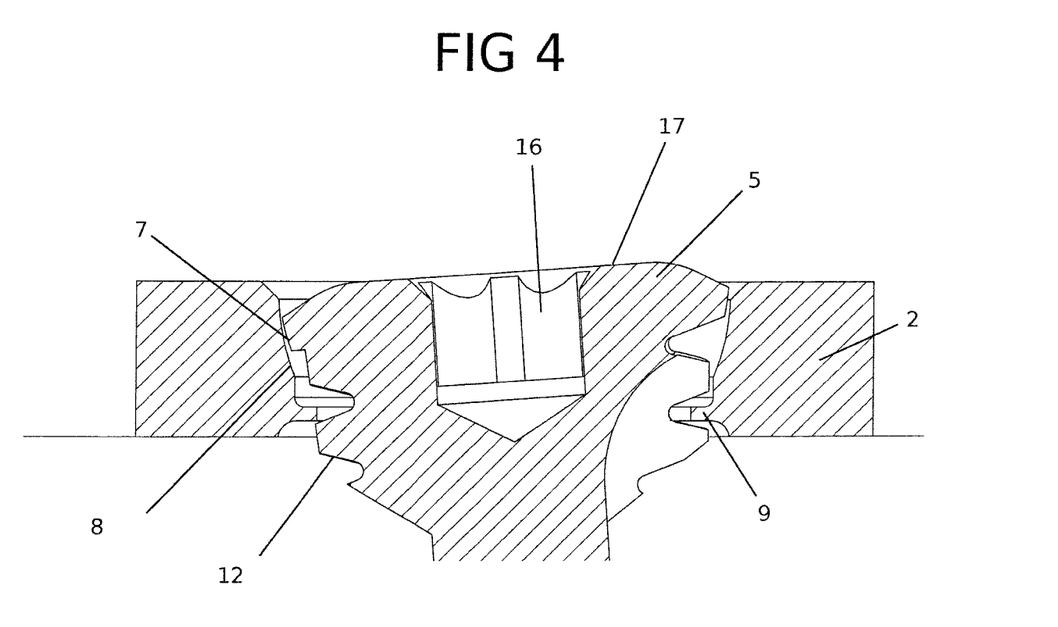
FIG. 4 is an enlarged detail view of the fastener portion of the FIG. 3 head.
Figure 5:
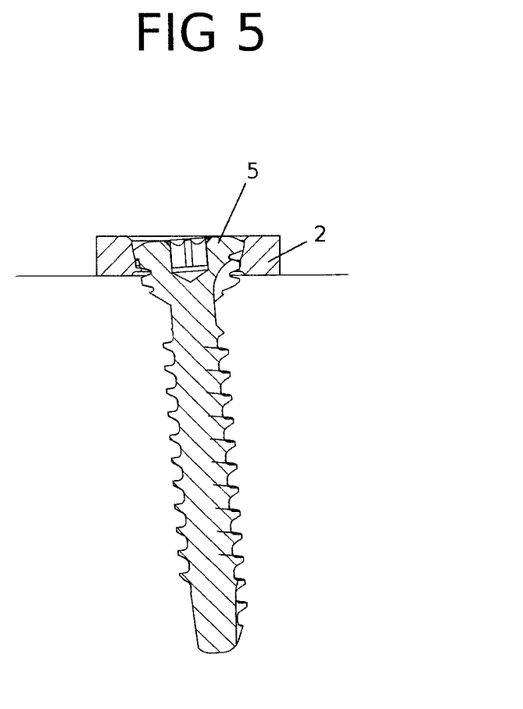
FIG. 5 is a section view of a screw when fully inserted in the orifice in a plate, during a screwdriving operation, the male and female spherical surfaces being in bearing contact and the inner collar having been tapped.
Figure 6:
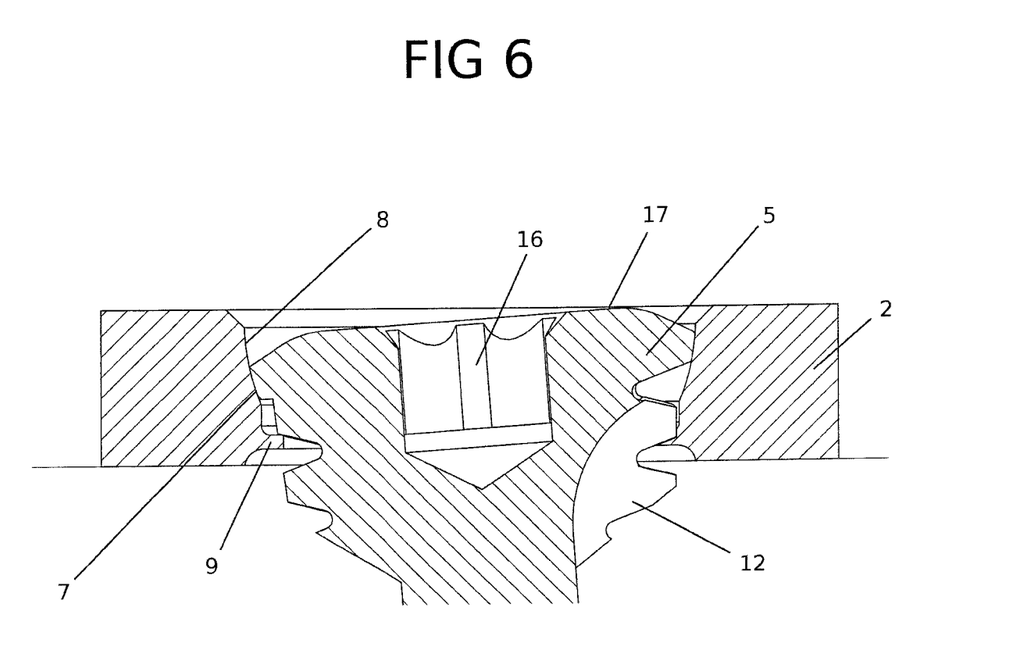
FIG. 6 is an enlarged detail view of the fastener portion of the FIG. 5 head.
Figure 7:
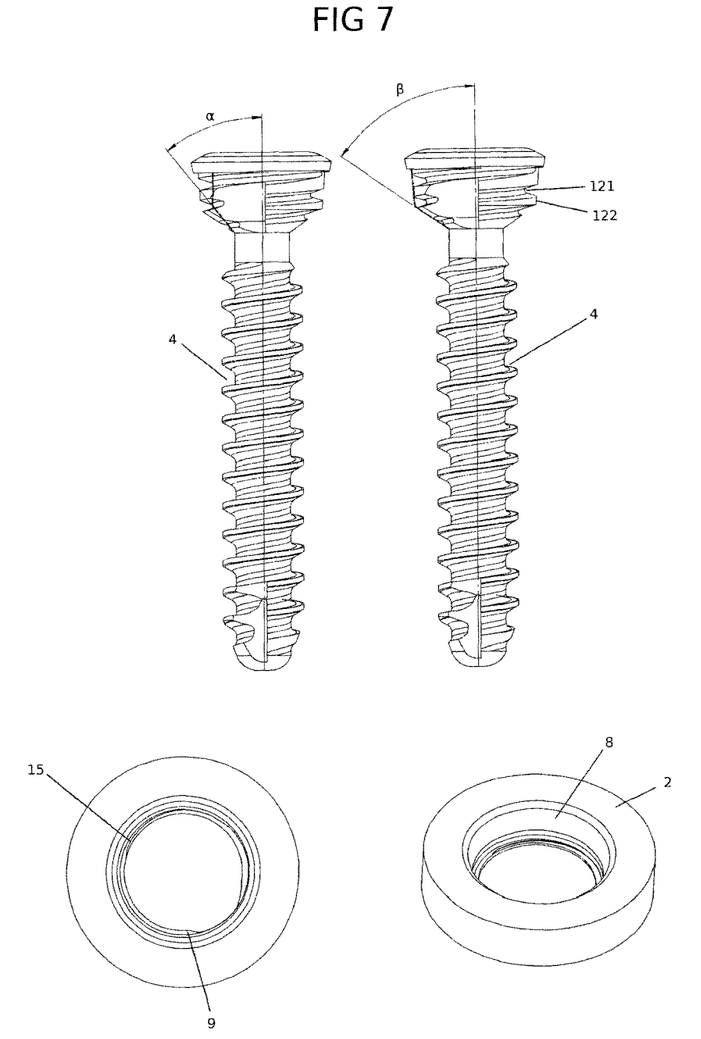
FIG. 7 is a diagrammatic view of two screws and two plates with the collar in the tapped state.
Figure 8:
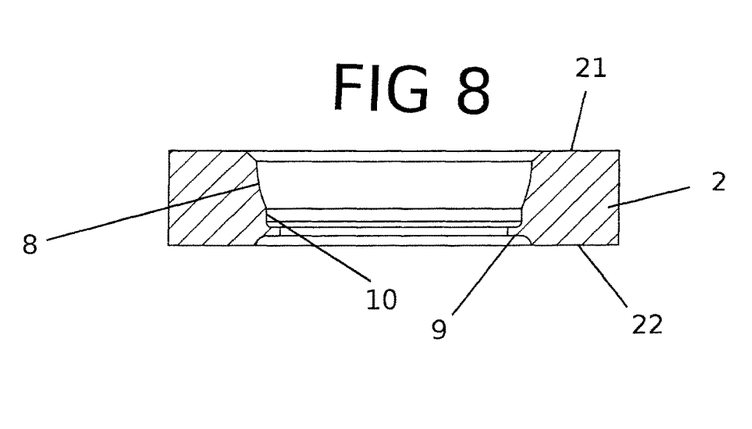
FIG. 8 is a section view of a plate before the inner collar is tapped.
Figure 9:
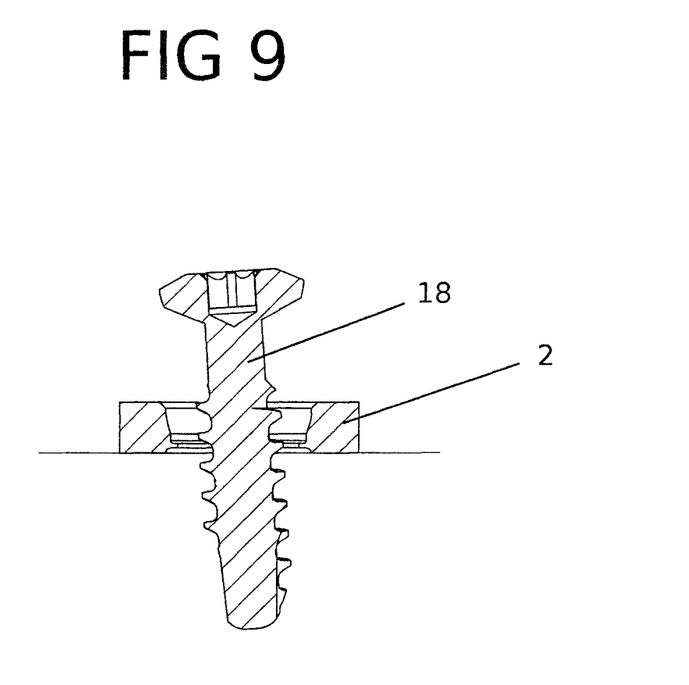
FIG. 9 is a section view of a screw when partially inserted in the orifice in a plate, during a screwdriving operation, said screw being a compression screw.

FIG. 9 shows another type of screw given reference 18 and suitable for use with the plate, in particular when the plate presents a plurality of through orifices 3. This screw differs from the screw shown in the other figures by the absence of a threaded portion at the head. This screw is thus merely a compression screw and not a locking screw as in the other examples. This figure shows the fact that the device may include not only at least one so-called "locking" fastener screw, but also a so-called "compression" fastener screw that differs from the locking fastener screw by the absence of the threaded portion at the screw head.

Such a device is thus fastened as follows: the plate is positioned to press against the bone. The surgeon proceeds, through the plate, to drill a hole in the bone using a drill jig. The drilling axis is selected to obtain a direction for the screw such that it can withstand large pull-out forces. The screw is then inserted through the plate along the axis of the hole and is screwed into the hole. While it is being screwed in, the threaded portion 12 of the screw taps the inner collar 9, thereby making a helical groove in said collar 9. The screw continues to be driven until it is put into abutment by co-operation between the male and female spherical surfaces. After reaching abutment, continued driving of the screw causes the threaded portion of the screw head to become jammed with the inner collar, thereby greatly increasing the effects and the sensation of locking. The cylindrical portion 10 of the bore in the orifice is configured, i.e. shaped and dimensioned, so as to avoid any premature contact between the cutting edge of the threaded portion of the screw head and the inner collar 9 prior to coming into abutment by bearing contact between the spherical surfaces, so as to ensure that the collar is tapped at the end of the stroke of the screw head within the orifice in the plate immediately prior to coming into abutment.

The design of the assembly as described above enables the screw to be tightened and then unscrewed several times, thereby enabling the surgeon to remove a screw, where necessary, and then to reinsert it, including along an axis different from the axis of its first insertion.

The invention claimed is:

1. A polyaxial bone fastener assembly comprising:
a plate type support having a top face, a bottom face, and at least one through orifice; and
at least one fastener screw for fastening the plate to bone material, the screw comprising a head and a threaded body, the body of the screw being insertable from the top face of the plate into the associated orifice in the plate and being suitable for passing through the orifice in order to be screwed into the bone material, and the head being suitable for being held in the associated orifice in the plate by bearing contact between complementary spherical surfaces, one of which is said to be "male" and carried by the head and the other of which is said to be "female" and is provided in the associated orifice in the plate, the female spherical surface forming a seat within which the male spherical surface is suitable for bearing when the screw is inserted in the orifice through the top face of the plate;
wherein the bore of the orifice or of at least one of the orifices, in the plate and that is suitable for being associated with a fastener screw comprises, going from the bottom face towards the top face of the plate, at least one inner collar, a cylindrical portion, and the seat-forming female spherical surface, and in that the head of the associated fastener screw, or of at least one of the associated fastener screws, comprises, between its male spherical surface and a zone for connection to the body of the screw, a threaded portion having a single-start thread, the thread being interrupted in at least two zones that are spaced apart from each other around the head, each interruption zone in the thread providing at least one cutting edge suitable for machining, the inner collar in the associated orifice of the plate while the screw is being driven to turn inside said orifice until reaching a position of bearing contact between the male and female spherical surfaces.

2. The polyaxial bone fastener assembly according to claim 1, wherein the thread of the threaded portion of the screw head presents, going from the top of the screw head towards its zone connected to the screw body, a thread root defining a body of cylindrical shape followed by a body of conical shape.

3. The polyaxial bone fastener assembly according to claim 1, wherein the thread of the threaded portion of the screw head presents, going from the top of the screw head towards its zone connected to the screw body, a thread crest defining a body of cylindrical shape or of cylindrical-conical shape.

4. The polyaxial bone fastener assembly according to claim 1, wherein the pitch of the threaded portion of the screw head is less than or equal to the pitch of the threaded portion of the screw body.

5. The polyaxial bone fastener assembly according to claim 1, wherein the inner collar of the orifice in the plate presents, once machined by the head of the associated fastener screw, a groove that is helical.

6. The polyaxial bone fastener assembly according to claim 1, wherein each cutting edge extends over the full height of the threaded portion of the screw head.

7. The polyaxial bone fastener assembly according to claim 1, wherein the diameter of the hole defined by the inner collar is less than the outside diameter of the threaded portion of the screw head over at least a fraction of the length of said threaded portion measured along the longitudinal axis of the screw.

8. The polyaxial bone fastener assembly according to claim 1, wherein the fastener screw, in its end-of-stroke position inside the associated orifice of the plate, is in bearing contact via the male spherical surface of the screw head with the female spherical surface of said orifice, and is in screw engagement via the threaded portion of the screw head with the inner collar of said orifice.

9. The polyaxial bone fastener assembly according to claim 1, wherein the seat-forming female spherical surface of the orifice, or of at least one of the orifices, in the plate is a concave spherical surface with its concave side facing towards the top face of the plate in order to define a housing of generally hemispherical shape.

10. The polyaxial bone fastener assembly according to claim 1, wherein the top of the screw head is provided with a prismatic axial socket.

11. The polyaxial bone fastener assembly according to claim 1, wherein the plate and the or at least one of the fastener screw(s) are made of the same material, preferably the same metal or the same metal alloy.

12. The polyaxial bone fastener assembly according to claim 1, wherein the male spherical surface carried by the screw head is dimensioned to be received in the thickness of the plate inside the through orifice in the plate in an end-of-stroke bearing position between the male spherical surface of the screw head and the female spherical surface of the plate.

13. The polyaxial bone fastener assembly according to claim 1, wherein the thickness of the collar is less than 1 mm.

14. The polyaxial bone fastener assembly according to claim 1, wherein the total thickness of the plate is less than 3 mm.

* * * * *